(12) United States Patent
Lund et al.

(10) Patent No.: US 11,642,014 B2
(45) Date of Patent: May 9, 2023

(54) HANDLE FOR AN ENDOSCOPE

(71) Applicant: AMBU A/S, Ballerup (DK)

(72) Inventors: Jesper Grøndahl Lund, Ballerup (DK); Michael Kappler Hansen, Vallensbæk (DK)

(73) Assignee: AMBU A/S, Ballerup (DK)

( * ) Notice: Subject to any disclaimer, the term of this patent is extended or adjusted under 35 U.S.C. 154(b) by 821 days.

(21) Appl. No.: 16/491,906

(22) PCT Filed: Mar. 7, 2018

(86) PCT No.: PCT/EP2018/055603
§ 371 (c)(1),
(2) Date: Sep. 6, 2019

(87) PCT Pub. No.: WO2018/162556
PCT Pub. Date: Sep. 13, 2018

(65) Prior Publication Data
US 2021/0137355 A1    May 13, 2021

(30) Foreign Application Priority Data
Mar. 8, 2017 (DK) .......................... PA 2017 70167

(51) Int. Cl.
*A61B 1/005* (2006.01)
*A61B 1/00* (2006.01)
*A61B 1/012* (2006.01)

(52) U.S. Cl.
CPC .......... *A61B 1/0057* (2013.01); *A61B 1/0011* (2013.01); *A61B 1/0052* (2013.01); *A61B 1/012* (2013.01)

(58) Field of Classification Search
CPC ... A61B 1/0057; A61B 1/0011; A61B 1/0052; A61B 1/012
See application file for complete search history.

(56) References Cited

U.S. PATENT DOCUMENTS

| 609,570 A | 8/1898 | Bowden |
| 3,897,775 A | 8/1975 | Furihata |
| (Continued) | | |

FOREIGN PATENT DOCUMENTS

| CN | 101594816 | 12/2009 |
| CN | 202589652 | 8/2012 |
| (Continued) | | |

OTHER PUBLICATIONS

International Preliminary Report on Patentability received for PCT Patent Application No. PCT/EP2018/055603, dated Sep. 19, 2019, 8 pages.

(Continued)

*Primary Examiner* — Anh Tuan T Nguyen
*Assistant Examiner* — Rynae E Boler
(74) *Attorney, Agent, or Firm* — Faegre Drinker Biddle & Reath LLP

(57) ABSTRACT

A handle for endoscope including a handle housing, an operating member (7) accommodated in said handle housing, at least one guide tube (16) adapted for surrounding and supporting at least one pull wire (17), and an anchoring block (15). The anchoring block (15) comprises at least one bore (20) adapted for insertion of said at least one guide tube (16) and at least one inlet passage in fluid communication with said at least one bore.

17 Claims, 8 Drawing Sheets

(56) References Cited

U.S. PATENT DOCUMENTS

| | | | |
|---|---|---|---|
| 3,958,566 A | 5/1976 | Furihata | |
| 4,203,430 A | 5/1980 | Takahashi | |
| 4,483,326 A | 11/1984 | Yamaka et al. | |
| 4,745,908 A | 5/1988 | Wardle | |
| 4,832,473 A | 5/1989 | Ueda | |
| 4,905,666 A | 3/1990 | Fukuda | |
| 4,941,455 A | 7/1990 | Watanabe et al. | |
| 5,167,221 A | 12/1992 | Chikama | |
| 5,170,775 A | 12/1992 | Tagami | |
| 5,179,934 A | 1/1993 | Nagayoshi et al. | |
| 5,347,989 A | 9/1994 | Monroe et al. | |
| 5,462,527 A | 10/1995 | Stevens-Wright et al. | |
| 5,512,035 A | 4/1996 | Konstorum et al. | |
| 5,541,622 A | 7/1996 | Engle et al. | |
| 5,626,553 A | 5/1997 | Frassica et al. | |
| 5,643,174 A | 7/1997 | Yamamoto et al. | |
| 5,888,192 A | 3/1999 | Heimberger | |
| 5,913,816 A | 6/1999 | Sanders et al. | |
| 5,938,588 A | 8/1999 | Grabover et al. | |
| 6,117,071 A | 9/2000 | Ito et al. | |
| 6,210,337 B1 | 4/2001 | Dunham et al. | |
| 6,440,062 B1 | 8/2002 | Ouchi | |
| 6,569,086 B2 | 5/2003 | Motoki et al. | |
| 6,821,157 B2 | 11/2004 | Brändström et al. | |
| 6,829,498 B2 | 12/2004 | Kipke et al. | |
| 7,524,301 B2 | 4/2009 | DuBois et al. | |
| 7,591,784 B2 | 9/2009 | Butler | |
| 7,662,092 B2 | 2/2010 | Miyagi et al. | |
| 7,662,094 B2 | 2/2010 | Iddan | |
| 7,794,392 B2 | 9/2010 | Maruyama | |
| 8,449,530 B2 | 5/2013 | Bacher et al. | |
| 8,790,250 B2 | 7/2014 | Petersen et al. | |
| 8,821,389 B2 | 9/2014 | Yamane | |
| 9,125,582 B2 | 9/2015 | Petersen | |
| 9,162,036 B2 | 10/2015 | Caples et al. | |
| 9,345,462 B2 | 5/2016 | Weitzner et al. | |
| 9,421,071 B2 | 8/2016 | Smith et al. | |
| 9,693,759 B2 | 7/2017 | Seguy | |
| 9,968,241 B2 | 5/2018 | Iuel | |
| 10,149,605 B2 | 12/2018 | Petersen et al. | |
| 2001/0023313 A1 | 9/2001 | Ide | |
| 2001/0025135 A1 | 9/2001 | Naito et al. | |
| 2003/0092965 A1 | 5/2003 | Konomura et al. | |
| 2003/0212308 A1 | 11/2003 | Bendall | |
| 2004/0019256 A1 | 1/2004 | Cubb et al. | |
| 2004/0220449 A1 | 11/2004 | Zirps et al. | |
| 2005/0131279 A1 | 6/2005 | Boulais et al. | |
| 2005/0197536 A1 | 9/2005 | Banik et al. | |
| 2007/0232858 A1 | 10/2007 | Macnamara et al. | |
| 2007/0239311 A1 | 12/2007 | Sato | |
| 2007/0282167 A1 | 12/2007 | Barenboym et al. | |
| 2007/0299311 A1 | 12/2007 | Sato et al. | |
| 2008/0051694 A1 | 2/2008 | Kato | |
| 2008/0249362 A1 | 10/2008 | Jiang et al. | |
| 2008/0249483 A1 | 10/2008 | Slenker et al. | |
| 2009/0143647 A1 | 6/2009 | Banju | |
| 2009/0209945 A1 | 8/2009 | Lobl et al. | |
| 2010/0063512 A1 | 3/2010 | Braga et al. | |
| 2010/0121147 A1 | 5/2010 | Oskin et al. | |
| 2010/0249639 A1 | 9/2010 | Bhatt | |
| 2011/0257477 A1 | 10/2011 | McWeeney | |
| 2011/0306831 A1 | 12/2011 | Køhnke et al. | |
| 2012/0130160 A1 | 5/2012 | Borrye et al. | |
| 2012/0220828 A1 | 8/2012 | Iwasaki | |
| 2013/0137924 A1 | 5/2013 | Iwasaki et al. | |
| 2013/0172813 A1 | 7/2013 | Caples et al. | |
| 2013/0281782 A1 | 10/2013 | Zhou | |
| 2014/0046123 A1 | 2/2014 | Connors et al. | |
| 2015/0216644 A1 | 8/2015 | Cahill et al. | |
| 2015/0335227 A1 | 11/2015 | Jacobsen et al. | |
| 2015/0366436 A1* | 12/2015 | Iuel | A61B 1/00066 600/149 |
| 2016/0095585 A1* | 4/2016 | Zergiebel | A61B 34/74 606/1 |
| 2017/0251906 A1 | 9/2017 | Hatano | |
| 2018/0296068 A1 | 10/2018 | Matthison-Hansen et al. | |
| 2018/0296069 A1 | 10/2018 | Matthison-Hansen | |
| 2018/0303315 A1 | 10/2018 | Matthison-Hansen | |
| 2018/0303316 A1 | 10/2018 | Matthison-Hansen | |
| 2018/0303317 A1 | 10/2018 | Matthison-Hansen | |
| 2018/0303472 A1 | 10/2018 | Matthison-Hansen et al. | |
| 2018/0309908 A1 | 10/2018 | Matthison-Hansen et al. | |
| 2020/0229684 A1 | 7/2020 | Lund et al. | |
| 2021/0212557 A1 | 7/2021 | Weitzner et al. | |

FOREIGN PATENT DOCUMENTS

| | | | |
|---|---|---|---|
| CN | 103181819 | 7/2013 | |
| CN | 105050477 | 11/2015 | |
| CN | 106175652 | 7/2016 | |
| EP | 3447216 A1 | 2/2019 | |
| JP | H11216103 A | 8/1999 | |
| JP | 2003052618 A | 2/2003 | |
| JP | 2003-070727 A | 3/2003 | |
| JP | 2005237608 A | 9/2005 | |
| JP | 2016220882 A * | 12/2016 | ........... A61B 1/0052 |
| WO | WO 2010/066787 | 6/2010 | |
| WO | WO 2010/066789 | 6/2010 | |
| WO | 2013099390 A1 | 7/2013 | |
| WO | WO 2013/071938 | 8/2014 | |
| WO | WO 2014/127780 | 8/2014 | |
| WO | 2016/188538 A1 | 12/2016 | |
| WO | 2016192033 A1 | 12/2016 | |
| WO | WO 2016/188537 | 12/2016 | |
| WO | 2017167713 A1 | 10/2017 | |

OTHER PUBLICATIONS

Search Report in related Danish Application No. PA 2017 70167, dated May 2, 2017.
International Search Report and Written Opinion in related PCT Application No. PCT/EP2018/055603, dated Jun. 8, 2018.
Patkin, M., "A Check-List for Handle Design", 2001, Ergonomics Australia On-Line (http://ergonomics.uq.edu.au/eaol/handle.pdf).
First Office Action issued in Chinese Patent Application No. 201880014615.6, dated Jun. 2, 2021 (translation included).
Office Action in U.S. Appl. No. 16/487,718, dated May 3, 2022.
Second Office Action issued in Chinese Patent Application No. 201880014615.6, dated Nov. 4, 2021 (translation included).
Notice of Allowance issued in U.S. Appl. No. 16/487,718, dated Aug. 18, 2022.

* cited by examiner

HANDLE FOR AN ENDOSCOPE

CROSS-REFERENCE TO RELATED APPLICATIONS

This application is a National stage application filed under 35 U.S.C. § 371 of International Application No. PCT/EP2018/055603, filed on Mar. 7, 2018, which claims the benefit of Denmark Patent Application No. PA 2017 70167, filed on Mar. 8, 2017, which applications are incorporated herein by reference thereto.

TECHNICAL FIELD

The present invention relates to endoscopes in general and more specifically to means for maintaining a tensioned pull wire in an endoscope.

BACKGROUND OF THE DISCLOSURE

Endoscopes are well known devices for visually inspecting inaccessible places such as human body cavities. Typically, the endoscope comprises an elongated insertion tube with a handle at the proximal end as seen from the operator and visual inspections means, such as a built in camera, at the distal end of the elongated insertion tube. This convention of distal and proximal, proximal being the end closest to the operator and distal being the end remote from the operator, as used above for the endoscope in general will, where applicable, be adhered to for all parts throughout this description. Electrical wiring for the camera and other electronics such as LED lighting run along the inside of the elongated insertion tube from the handle to the tip at the distal end. Instead of using cameras, endoscopes may also be fibre-optic, in which case the optical fibres run along inside of the elongated insertion tube. Also, a working channel may run along the inside of the insertion tube from the handle to the tip, e.g. allowing liquid to be removed from the body cavity or allowing the insertion of surgical instruments or the like into the body cavity.

Furthermore, in order to be able to maneuver the endoscope inside the body cavity, the distal end of the endoscope may comprise a section with increased flexibility, e.g. an articulated tip part allowing the operator to bend this section. Typically, this is done by tensioning or slacking pull-wires in a guide tube also running along the inside of the elongated insertion tube from the articulated tip part to a control mechanism with a control knob in the handle in an arrangement commonly known as a Bowden cable.

The pull-wire running along the inside of the guide tube of a Bowden cable normally extends with a predetermined length over either end allowing an operating member to be attached to a free end, in the following referred to as the proximal end, and an operated member to be attached to the other free end, in the following referred to as the distal end. When the ends of the guide tube are held stationary, movement of the proximal end of the pull-wire with respect to the guide tube is transmitted to the distal end as a corresponding movement of the distal end of the pull-wire with respect to the guide tube, so as to effect a movement of the operated member.

One way of securing the proximal ends of the guide tubes is disclosed in WO2014/127780. Here, the proximal ends of the guide tubes are terminated in a termination block located in a seat or recess provided on the inside of the handle housing wall of the handle of the endoscope. More specifically, the proximal ends of the guide tubes are terminated in suitable bores in the termination block. More specifically the bores are stepped in order to provide a ledge which the end of a respective guide tube abuts, whereas the pull wire continues through the bore towards the operating member.

Another way of securing the proximal ends of the guide tubes is disclosed in WO2010/066789. Here the proximal ends of the guide tubes terminate at a pillar protruding from the inside of the handle housing wall into the interior of the handle. It is stated that the termination directs the cables towards their attachment points at the operating member, but no details of the termination and of how this is achieved are disclosed.

Furthermore, U.S. Pat. No. 3,897,775 describes a multiple use endoscope having an anchoring block in which two pairs of pipes are secured in four bores in a manner not disclosed or otherwise indicated.

SUMMARY OF THE DISCLOSURE

Based on this prior art it is the object of the present invention to provide an improved way of securing the end of a guide tube in a given position with respect to the operating member of an endoscope, in particular with respect to the handle housing in which the operating member is accommodated.

According to a first aspect of the present invention this object is achieved by a handle for an endoscope, said handle comprising, a handle housing, an operating member accommodated in said handle, at least one guide tube adapted for surrounding and supporting at least one pull wire over a first part of the length of the pull wire, an anchoring block for securing at least one part of the guide tube in a predetermined position with respect to the operating member, said anchoring block comprising at least one bore adapted for insertion of said at least one guide tube, wherein said anchoring block comprises at least one inlet passage in fluid communication with said at least one bore.

According to a second aspect of the present invention this object is achieved by an endoscope having a handle comprising, a handle housing, an operating member accommodated in said handle, at least one guide tube adapted for surrounding and supporting at least one pull wire over a first part of the length of the pull wire, an anchoring block for securing at least one part of the guide tube in a predetermined position with respect to the operating member, said anchoring block comprising at least one bore adapted for insertion of said at least one guide tube, wherein said anchoring block comprises at least one inlet passage in fluid communication with said at least one bore.

By providing such an anchoring block it becomes very easy during manufacture to position the free end of the guide tube with respect to the handle and, in turn, the operating member to which the pull wire is attached. At the same time it becomes very easy to secure the free end of the guide tube in this position by pouring a correct amount of a suitable glue or adhesive into the anchoring block. Furthermore, the use of glued parts in this way renders the entire construction of the endoscope more suitable for single use because parts that in a reusable endoscope would have to be mounted in a detachable manner for replacement may simply be secured by gluing. Thus, complicated constructions for allowing the detachment and replacement are avoided.

According to a first embodiment of the present invention, the at least one bore is a through bore allowing the through passage of the guide tube. This allows the free end of the guide tube to visibly protrude from the anchoring block towards the operating member, in turn allowing verification of the proper insertion of the guide tube into the anchoring block.

According to another embodiment of the present invention, the anchoring block comprises a transparent or translucent plastic material. This allows for the use of a glue or a resin which will cure or set under irradiation with light, in particular ultra violet light. In a further specific embodiment the anchoring block is made from one material which is transparent or translucent.

According to a further embodiment, the handle housing comprises a receptacle adapted for accommodating the anchoring block. This allows the provision of the anchoring block as a separately manufactured item, in turn, facilitating both the manufacture thereof and the handle housing, as compared to the manufacture of the anchoring block as an integral part of the handle housing.

According to a preferred embodiment, the anchoring block is adapted for insertion into the receptacle in the handle housing. Adapting it for insertion, allows the easy placement of the anchoring block in the receptacle.

According to a further preferred embodiment, the receptacle is formed integrally with the handle housing. This allows good control of the position of the anchoring block with respect to the operating member when correctly inserted into the receptacle.

According to an especially preferred embodiment, the anchoring block comprises an essentially cylindrical protrusion. This, cylindrical protrusion is advantageous when during assembly of the endoscope correct tension has to be applied to the pull wire.

BRIEF DESCRIPTION OF THE DRAWINGS

The invention will now be explained in greater detail based on non-limiting exemplary embodiments, and with reference to the drawings on which.

DETAILED DESCRIPTION

Figure 1:
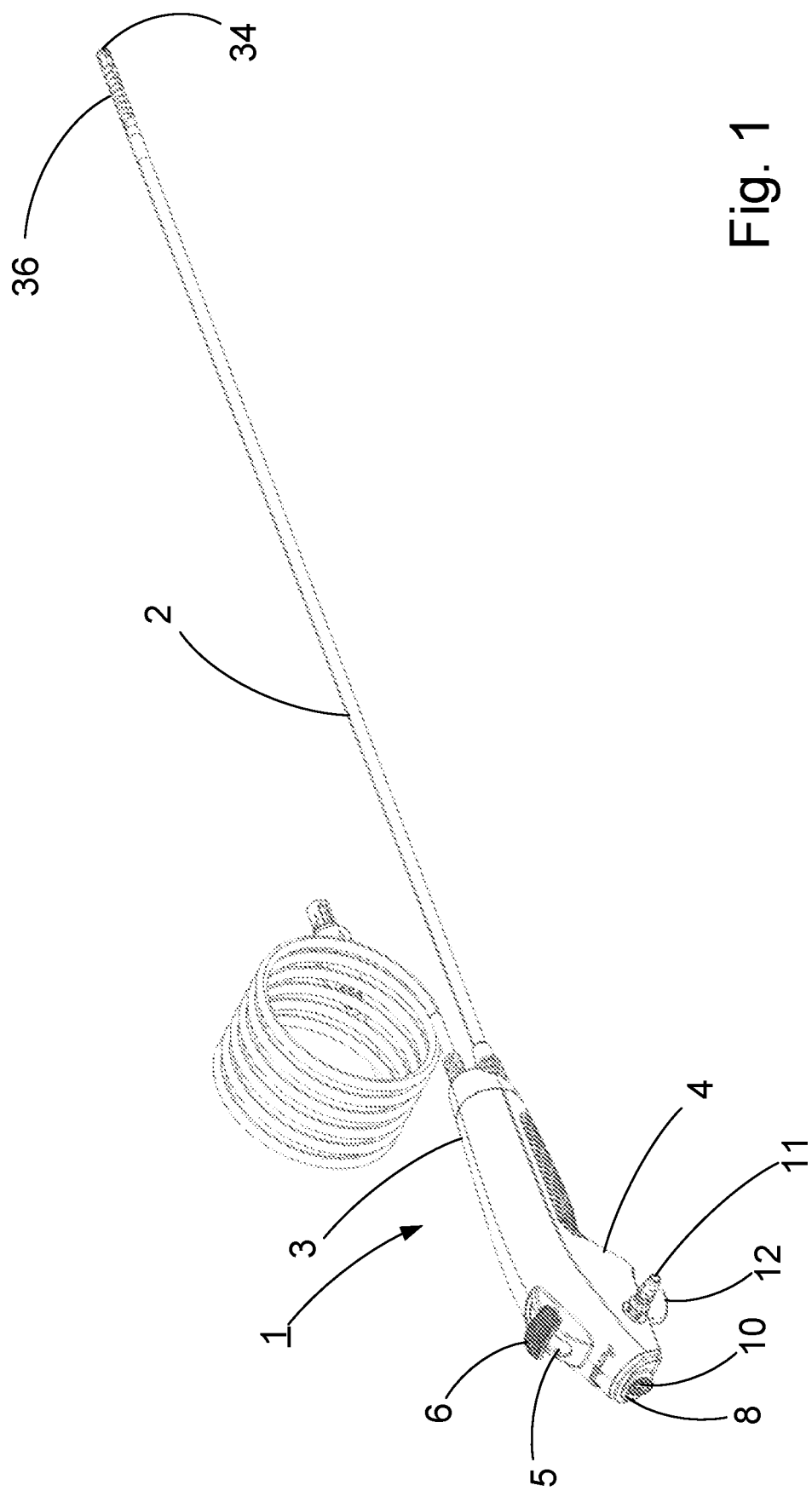
FIG. 1 shows a perspective view of an endoscope with a handle according to the present invention.
Figure 2:
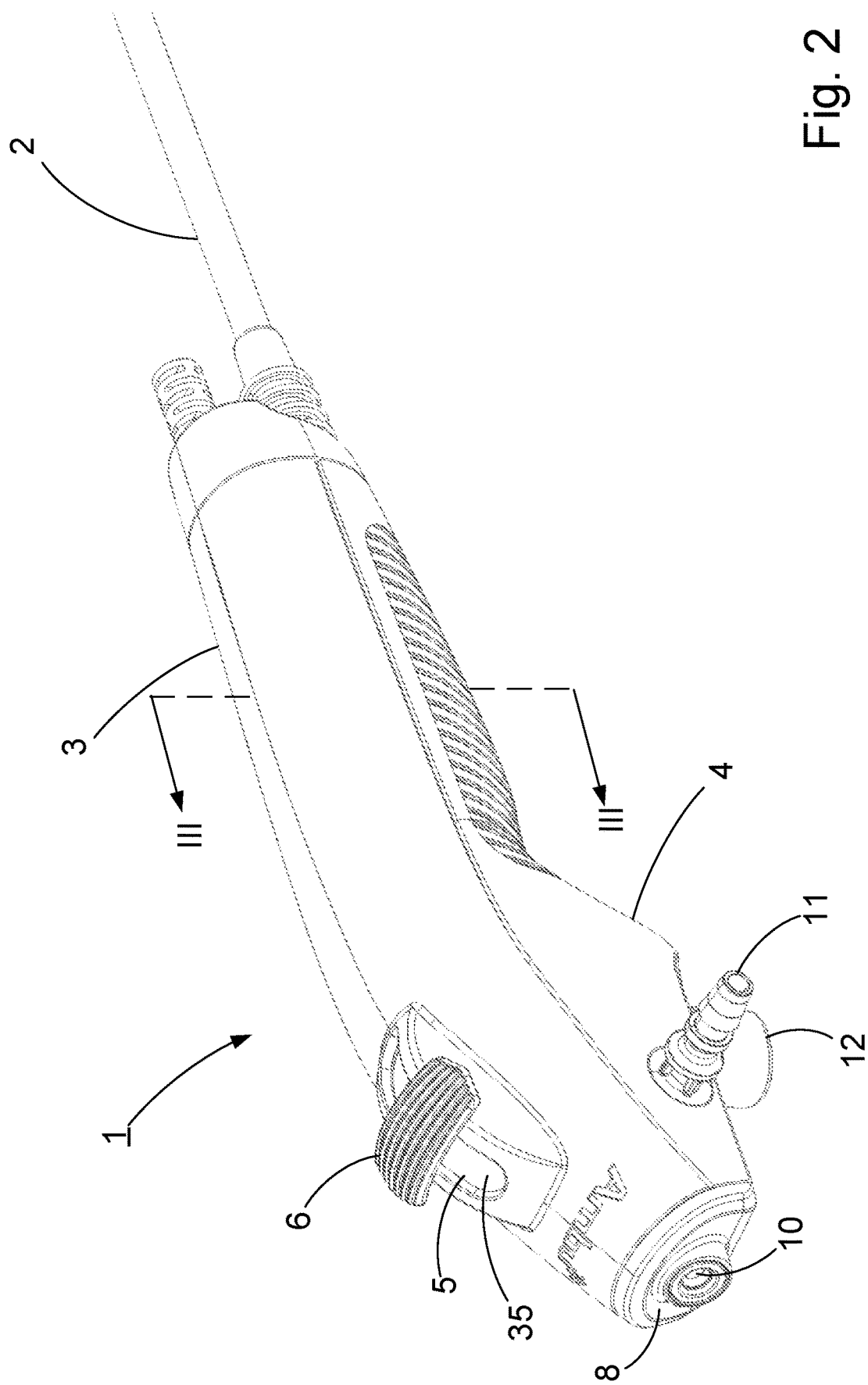
FIG. 2 shows a perspective view of a handle of an endoscope in accordance with the present invention.

Turning first to FIG. 2 a perspective view of a handle 1 of an endoscope according to the invention is shown. From the handle an insertion tube 2 extends. The insertion tube 2 is shown only in part in FIG. 2 as the details thereof are not of importance for the present invention, and as such well known in the art. A general overview is seen in FIG. 1. Details of the insertion tube may e.g. be found in the aforementioned WO2014/127780 incorporated herein by reference. The handle 1 comprises a handle housing with lid part 3 and a main body part 4 and a number of minor housing parts. The lid part 3 comprises an elongate aperture 5 through which a control knob 6 of an operating member 7 protrudes at an angle to the lid, so as to allow it to be readily manipulated by a thumb of an operator. The operating member 7 is not itself visible in FIG. 2, but the shield 35 thereof is visible through the aperture 5. The main body part 4 is adapted to accommodate most of the internal parts of the endoscope handle, fixed as well as movable, such as the aforementioned operating member 7. When closed by the lid part 3 the main body part 4 and the lid part 3 form a generally tubular handle housing. The handle housing is further closed at the proximal end of the endoscope by an end piece 8. At the opposite end, the tubular handle housing is closed by a transition part 9 providing the transition from the handle 1 to the insertion tube 2. The end piece 8 is preferably provided with and access port 10 for an internal working channel 14 (not visible in FIG. 2) leading to the distal tip 34 (shown only in FIG. 1) of the endoscope in a well-known manner. The main body part 4 also preferably accommodates a lead-in 11 for connecting a vacuum suction hose to an internal suction channel 13 (also not visible in FIG. 2) in the endoscope, in a likewise well-known manner, as well as a push-button 12 controlling a valve for activation of the suction from the distal end of the insertion tube 2 though the suction channel 13 of the endoscope.

Figure 3:
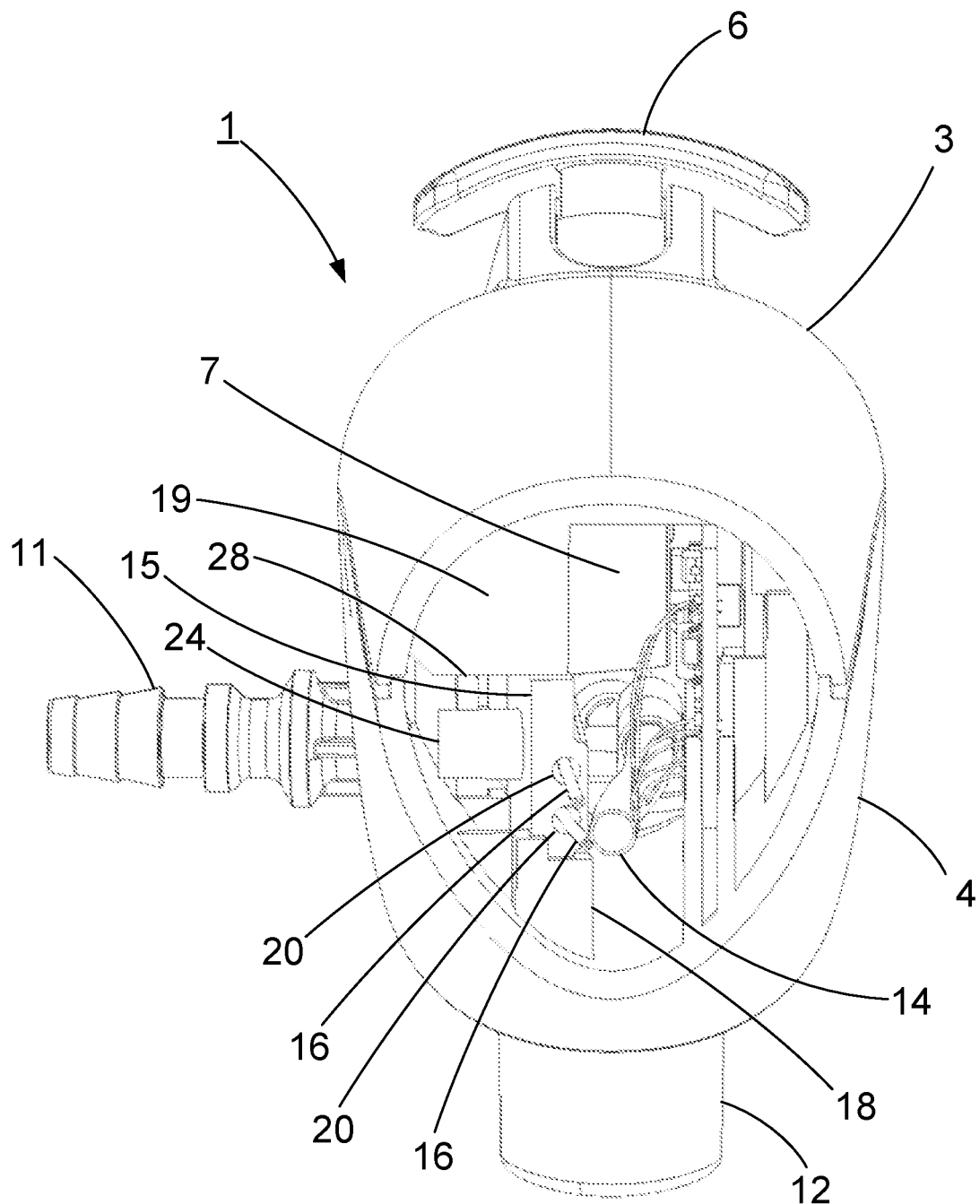
FIG. 3 shows a cross-sectional view of the handle of FIG. 2 taken along the line III-III.

Turning now to the cross-section in FIG. 3 some of the internal parts accommodated in and held by the main body part 4 of the handle housing can be seen. These parts include inter alia the already mentioned operating member 7 and the working channel 14, but also an anchoring block 15 for the guide tubes 16 of pull wires 17 of the Bowden cables leading from the operating member 7 to an articulated distal tip part 36 (shown only in FIG. 1) of the endoscope at the distal end of the insertion tube. The details of the articulated distal tip part 36 are well-known in the art and not as such of interest in the present invention, and will therefore not be described in detail. An example is found in the aforementioned WO2014/127780. In the preferred embodiment there are two pull wires 17, but the skilled person will know that there may be only one, but also more than two, e.g. three or four.

In the preferred embodiment shown, the anchoring block 15 is a separate element held in a fixed position with respect to the handle housing, by a receptacle 18 into which it is inserted. The receptacle 18 is preferably formed integrally with the main body part 4, more specifically as one or more protrusions on the inside wall thereof. The anchoring block 15 may be secured in the receptacle by means of adhesive or the like, or it may simply be clamped by one or more suitably engaging protrusions or the like, provided on the inside wall of the lid part 3, when the latter is in position. As can be seen from FIG. 3, in the illustrated preferred embodiment only a single engaging protrusion is provided in the form of a cross-rib 19 extending perpendicular from the inside wall of the lid part 3. To further ensure the position of the anchoring block 15 in the receptacle 18, the anchoring block 15 may comprise guide means in the form of grooves 25 (see FIG. 6) adapted to engage corresponding ribs provided on the inside wall of the main body part 4. The anchoring block 15 in a preferred embodiment comprises a main body member, generally in the shape of a rectangular or square, i.e. a tile or a slab with two opposite large sides and four smaller sides connecting the large sides. Generally, the pairs of opposite sides are parallel to each other, but to ensure the correct position it is preferred that one side 26 is adapted to engage inside wall of the main body part, and therefore has a matching curvature and angle. The angle provides a wedge which not only facilitates the insertion into the receptacle, but also indicates to the assembling person, the correct orientation of the anchoring block when it is inserted into the receptacle.

The anchoring block 15 comprises at least a number of bores 20 corresponding to the number of Bowden cables used in the specific endoscope, i.e. two in the present embodiment. The bores 20 are through bores and generally have an internal diameter allowing the guide tubes 16 to pass all the way through so that the proximal end of the guide tubes 16 protrude visibly from the anchoring block 15. It would of course also be possibly to have through bores with varying diameter, in particular stepped, so as to allow the guide tubes 16 to abut a ledge in the bore 20 inside of the anchoring block 15, so that only the pull wires pass all the way through the anchoring block 15. This offers the advantage of securing the guide tubes 16 even better to the anchoring block 15. This, however, is considered less desirable because it entails the risk of introducing unnecessary friction from the anchoring block 15, which, unlike the guide tubes 16, is not necessarily optimized for low friction.

As can be seen in FIGS. 3-7, the diameter of the bore 20 generally exceeds the outer diameter of the guide tube 16. This allows plenty of room for an adhesive in the form of glue such as a curable resin to enter and secure the guide tube 16 with respect to the anchoring block 15.

Turning now to FIG. 2-7, the main body part 4 with the anchoring block 15 is shown at another angle. From this angle it can be seen that in the anchoring block 15 a cut-out 21a is formed. The cut-out 21a leads to the bore 20 and thus provides an inlet passage 21 in fluid communication with the bore 20. The inlet passage 21 is located more or less in the middle of the length of the bore 20. This allows the adhesive for securing the guide tube 16 to be simply poured into the bore 20, distribute itself around the guide tube 16 and in either direction towards the openings 20a, 20b, in distal and proximal surfaces 15a, 15b of the anchoring block 15 (i.e. for each bore 20, a first opening 20a in the distal surface 15a and a second opening 15b in the proximal surface 15b), at the respective ends of the bore 20. When the adhesive sets, the guide tube 16 is secured with respect to the anchoring block 15. Because the anchoring block 15 is inserted and held in the receptacle formed on the inside wall of the main body 4 the guide tube 16 is fixed with in a predetermined, desired position with respect to the handle housing and, in turn, with respect to the operating member 7. The adhesive is preferably an UV curable resin, curing under the irradiation with ultra violet light (UV). Accordingly, the anchoring block is preferably made of a transparent or translucent material, in particular a transparent or translucent plastic material.

Figure 5:
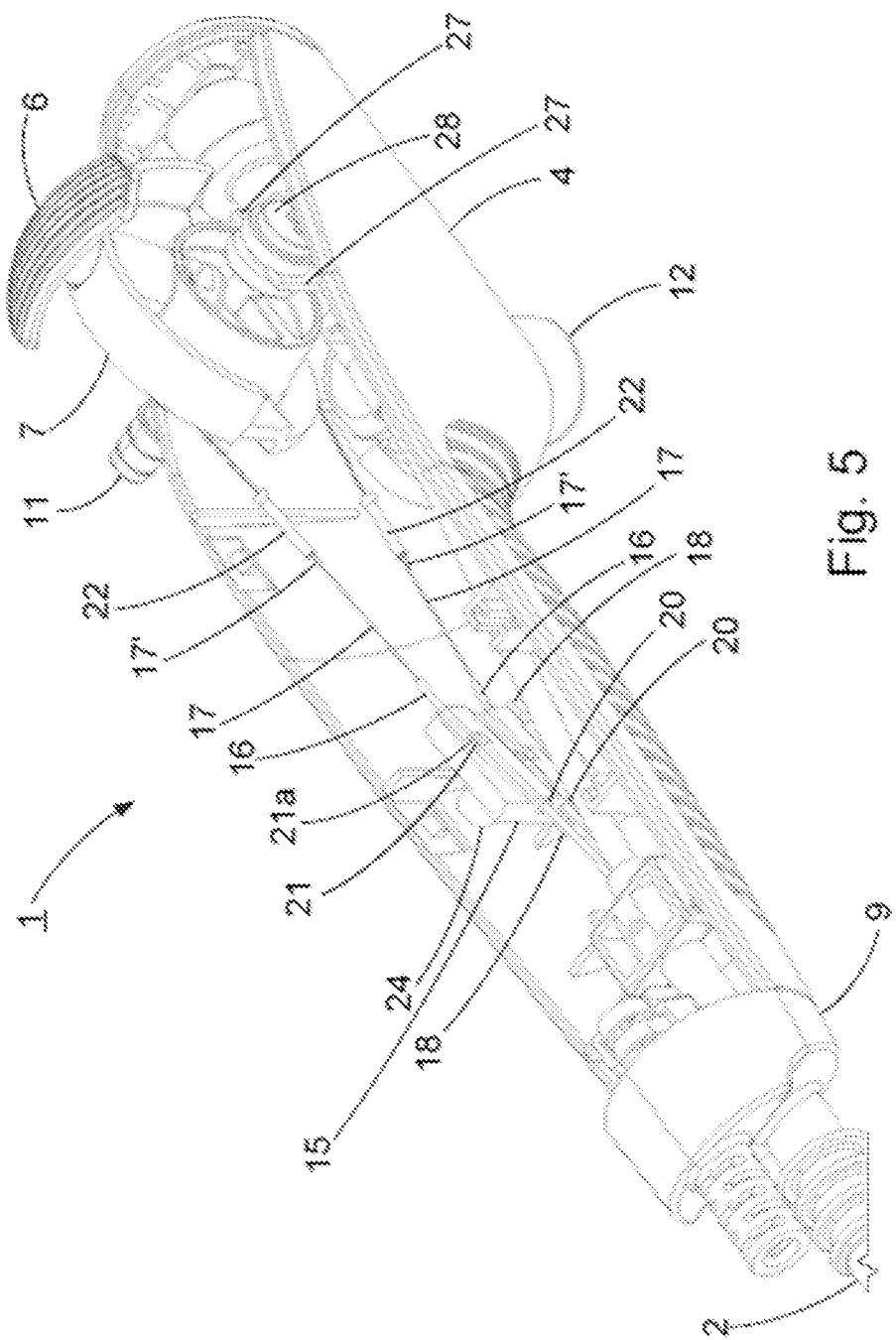
FIG. 5 shows another perspective view of the handle of FIG. 2 with the handle housing removed as in FIG. 3 for another view to the internal parts.
Figure 6:
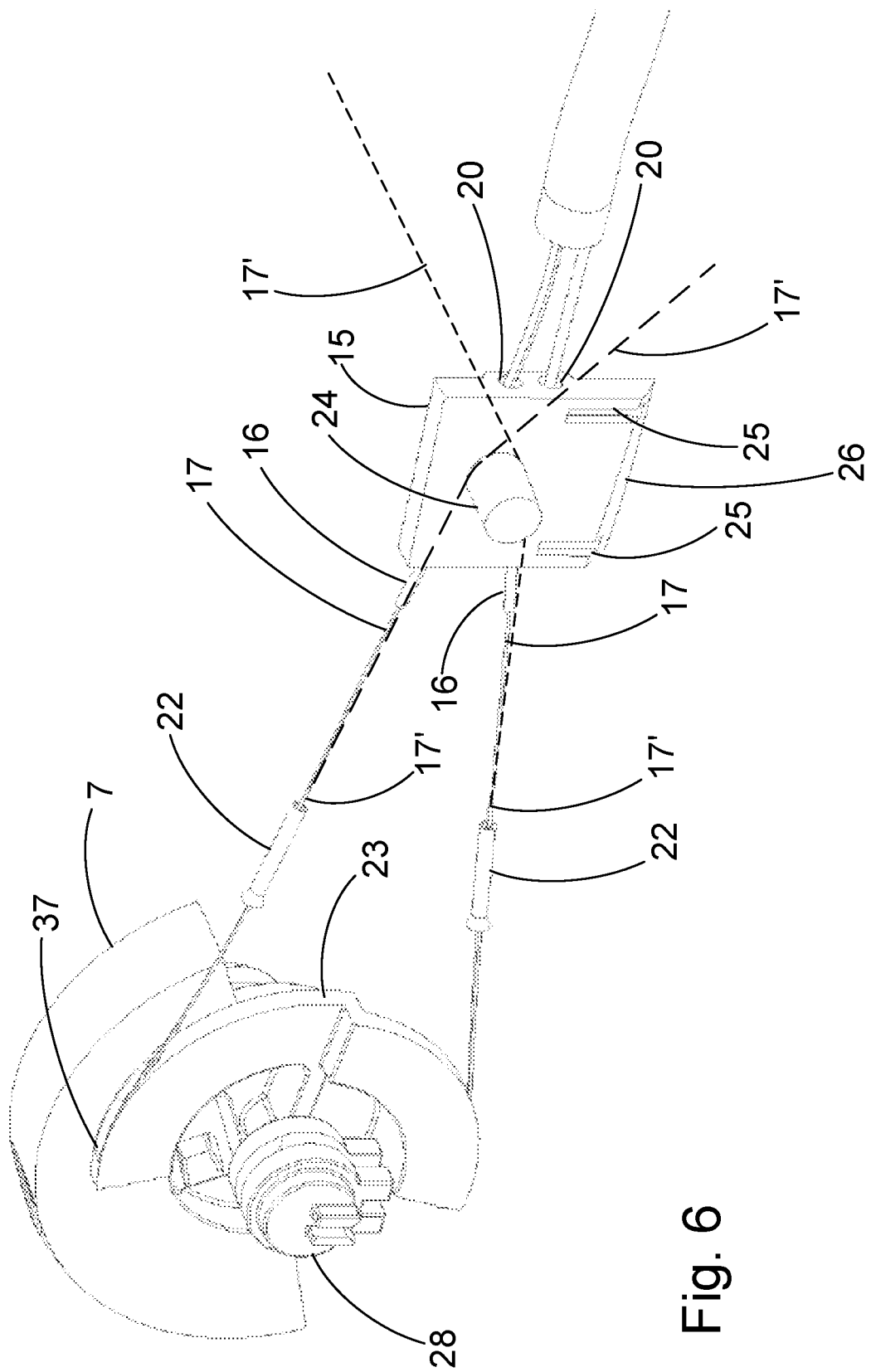
FIG. 6 shows a perspective view of the anchoring block with the Bowden cables and the operating member to which they are attached.

As can be seen from FIGS. 5 and 6 the orientation of the bore 20 in the anchoring block is carefully selected to point the guide tube 16 towards an attachment point 37 at the operating member 7, when the anchoring block 15 is correctly inserted in the receptacle 18.

With the guide tube 16 properly secured in the correct orientation in the anchoring block 15 the guide tube 16 may be cut at a suitable point and the remainder removed so as to leave the pull wire 17 inside uncovered. The point where the guide tube 16 is cut now provides the free proximal end of the guide tube 16. A small part of the guide tube is protruding from the anchoring block 15, i.e. between the anchoring block 15 and the proximal end of the guide tube 16. Accordingly, an uncovered length of the pull wire 17 now extends from the proximal end of the guide tube 16.

Since the proximal end of the guide tube 16 points towards the attachment point 37 the pull wire may be drawn to the attachment point 37 in a generally straight line forming a tangent to the outer cylindrical surface 23 of the operating member 7, and in particular without any kinks or discontinuities at the proximal end of the guide tube 16. Such kinks or discontinuities could increase wear on the guide tube 16, the pull wires 17 or even the anchoring block 15, but are thus avoided. Moreover, because the short length of guide tube 16 extends from the anchoring block in the right direction it is of less importance where exactly the guide tube is cut, thus facilitating and speeding the manual assembly process of the handle. Because precision it not so important, it may instead be advantageous to cut the guide tube 16 to length before it is secured, or even inserted, in the anchoring block 15.

Figure 4:
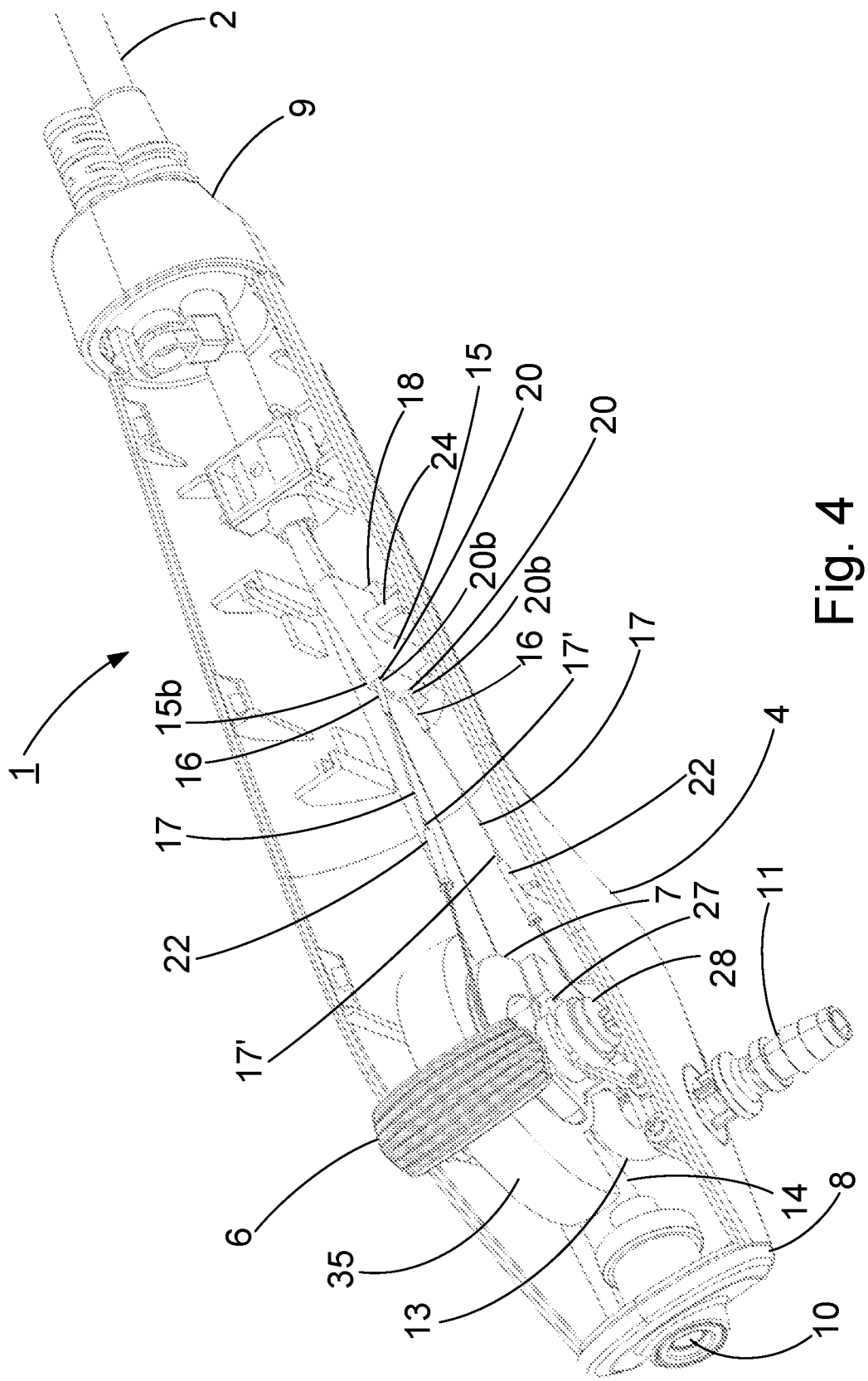
FIG. 4 shows a perspective view of the handle of FIG. 2 with a handle housing part removed for a better view of the internal parts.

At the attachment point 37 the pull wire 17 is attached to the operating member 7. From the attachment point 37 there is a transition surface onto an outer cylindrical surface 23. The cylindrical surface ensures that when the operating member is turned, the pulling force remains proportional to the torque applied to the control knob 6, and at the same time maintains the desired direction of the pull wire 17 towards the proximal end of the guide tube 16. It also aids in securing the attachment of the pull wire 17 to the operating member 7. More specifically, a loop is preferably formed by drawing the remainder 17' of the pull wire 17 back along itself towards the proximal end of the guide tube 16 attaching the remainder 17' of the pull wire to the pull wire 17 itself, somewhere between the operation member 7 and the proximal end of the guide tube 16 as best seen in FIGS. 4 and 5. Attachment by crimping using an open or closed tube 22 is preferred, but the skilled person will know that other methods of attaching the pull wire 17 to itself could be used instead. Apart from the transition the outer cylindrical surface 23 is preferably smooth, i.e. without any grooves. Not having any groove maximizes the diameter of the cylindrical surface 23 and hence the lever, in turn, maximizing the displacement of the pull wire 17 and consequently the maximum deflection of the articulated tip part 36.

For the proper function of the Bowden cable in the operation of the articulated tip part, it is of importance to have good control over the tension of the pull wires 17. Both slack and over tension is undesired.

For this, the endoscope comprises a direction guide 24. In the preferred embodiment the direction guide 24 is a cylindrical protrusion formed integrally with the anchoring block 15, and thus in vicinity of the first location where the guide tube 16 is fixed with respect to the handle housing. As mentioned, the anchoring block 15 in preferred embodiment is generally a rectangular or square body member, i.e. a tile or a slab with two opposite large sides and four smaller sides connecting the large sides. As can best be seen in FIG. 5 the cylindrical protrusion extends perpendicular from one of the large sides whereas the inlet passages 21 to the bores 20 are located on the opposite one of the large sides. The bores 20 extend between two of the smaller sides in a first plane between and generally parallel with the large sides. The bores 20 generally extend at an angle to each other so that each bore points towards a respective connection point 37 on either side of the diameter of the operation member 7. The outer surface of the direction guide 24 comprises an outer surface extending essentially perpendicular to the first plane in which the at least one pull wire lies. In the preferred embodiment the mantle of the cylinder thus extends perpendicular to the large sides, and the first plane in which the bores 20 lie.

The projection of the mantle onto the first plane preferably coincides with the through bores 20. If the bores 20 are straight, they thus form tangents to the circular projection of the mantle onto the first plane. It should however be noted that the bores 20 could be curved, and in that case the imaginary linear extension of the linear part of the pull wire 17 between the operating member and the proximal end of the guide tubes 16 should be tangential to the projection of the direction guide 24.

During the assembly of the endoscope, the direction guide 24 serves to keep the direction and the tension on the part of the pull wire 17 which is drawn back along itself, i.e. the remainder 17'. More specifically the free end of the pull wire 17 is drawn past direction guide 24 and partially around it to secure the straight line from the attachment point 37 to the direction guide 24. This is indicated by showing the remainder 17' which will later be cut away, with the dashed lines in FIG. 6. From the direction guide 24 it is the remainder 17' of the pull wire 17 drawn in another direction to a tensioning device where it is temporarily attached. The tensioning device ensures that the correct tension is on the pull wire 17 when the loop is secured by attaching the pull wire 17 to itself, e.g. by crimping the tube 22 onto it. Typical values of tension would be in the range of 1 N to 4 N. Also, the clamping mechanism leaves both hands of the assembly person free for the crimping operation etc. The free end of the pull wire 17 is then severed, and the remainder of the pull wire, i.e. the unused may be released from the clamping means. Preferably, one and the same direction guide 24 may be used for both pull wires 17. That is to say the diameter of the cylinder is adapted to match the location of both bores 20, so that for one bore 20 the pull wire 17 is drawn partially around the direction guide 24 in a clockwise sense, and for the other bore 20 the pull wire 17 is drawn partially around the direction guide 24 in the counter-clockwise sense. It is of course also possible to use more direction guides, e.g. one per bore 20. Furthermore, it is of course not excluded to use only one direction guide 24 and draw both the pull wires around it in the same direction. This of course would give a less accurate direction of the pull wires during attachment, but in some configurations this tradeoff may be acceptable. One such configuration could be a direction guide 24 with a smaller diameter of the cylinder, not matching any of the locations of the bores 20.

Figure 7:
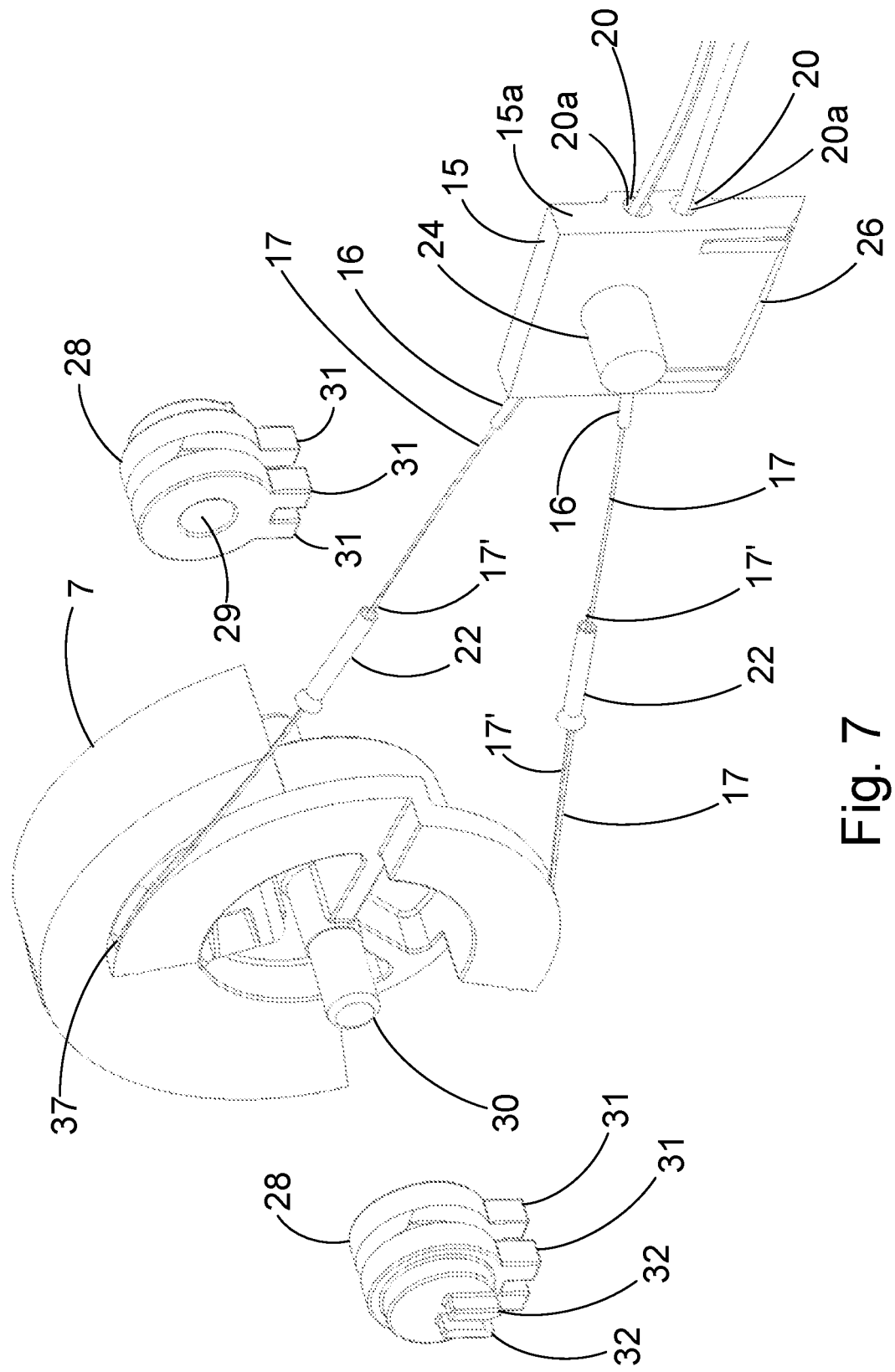
FIG. 7 shows a partially exploded view of details of the bearings of the operating member.
Figure 8:
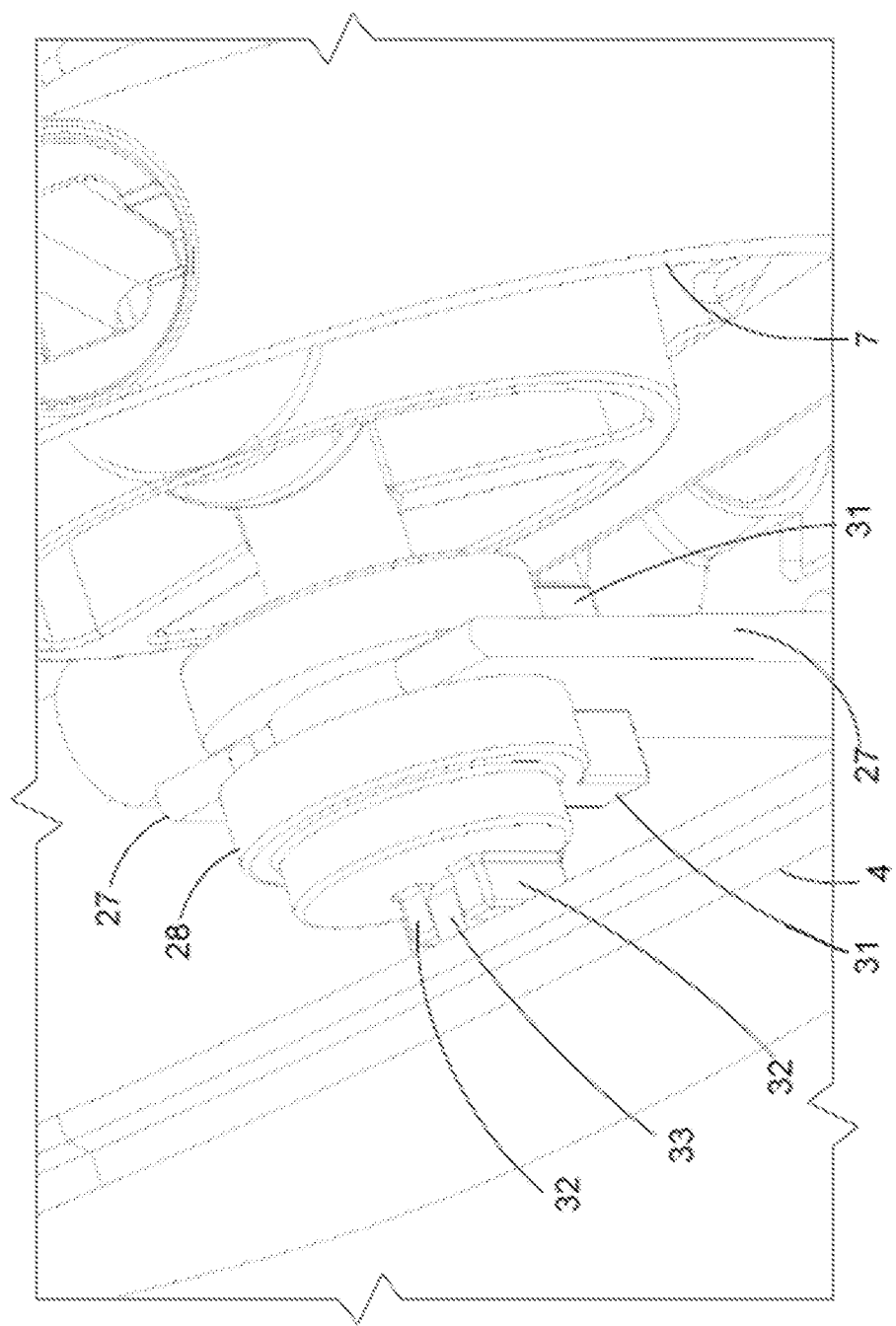
FIG. 8 shows details of the mounting of the operating members and the bearings in the handle housing.

According to a further preferred embodiment the operating member may be held in a novel bearing arrangement. This novel bearing arrangement, which is best seen in FIGS. 6 to 8, may be implemented in an endoscope handle independently of the way the guide tube 16 is secured to the handle housing and the full wires tensioned and directed towards the operating member.

Turning, however, first to FIG. 5 a bifurcated post 27 can be seen. Another similar bifurcated post 27 visible in FIG. 8 is arranged on the other side of the operating member 7. The bifurcation of the post 27 is provided by a recess provided in the free end of each post. The recess is adapted to receive a bearing element 28 made from a suitable low friction material, i.e. selected to provide low friction for the shaft 30 of the operating member 7. One example of a suitable material could be POM (Polyoxymethylene). The bearing element 28 has a blind cylindrical hole 29 adapted to receive one end of the shaft 30 of the operating member. The shaft 30 is preferably made integrally with the operating member 7 and of the same material, e.g. by injection molding, so that it rotates with the operating member 7. The bearing element 28 has suitable protrusion 31 engaging on either side of the bifurcated post 27 so as to prevent translatory movement with respect to the bifurcated post 27 in the axial direction of the shaft 30. Alternatively or additionally, the bearing member has suitable protrusions 32 engaging on either side of a rib 33 provided on the inside wall of the main body part 4. The engagement between the protrusions 32 and the rib 33 prevents rotary movement of the bearing element 28 with respect to the main body part 4 and in particular with respect to the bifurcated post 27. It is thus ensured that the shaft 30 does not rotate the bearing element 28, but rather rotates itself in the bearing element 28 so that the selected frictional properties are utilized in full. If not, unnecessary noise and undesired tactile feedback could be produced when the operating member 7 is turned by the thumb of the operator, in turn, leading to a sensation of reduced quality of the endoscope for the operator.

For the same reason the dimensions of the shaft 30 and the bearing elements 28 are carefully taken into account in order to prevent any play. More specifically the length of the shaft 30 is slightly longer than the distance between the bottoms of the blind holes 29 in the bearing elements 28 when the latter are properly located in the bifurcated posts 27. Thus the bifurcated posts 27 will be bent slightly away from the operating member 7 in an elastic manner leaving no play between the shaft 30 and the bearing elements 28. Likewise, the dimensions of the part of the bearing elements 28 located between the bifurcated posts 27 and the main body part 4 is also slightly larger than the distance between the inside wall of the main body part 4 and the bearing part where they engage each other, so that the bearing elements 28 press walls of the main body parts slightly apart in the assembled state. The elasticity of the main body part 4 thus aids in pressing the bearing elements 28 into the engagement with the shaft 30.

The skilled person will understand that the invention as described above is not limited to the exemplary embodiments but many variations and implementations are possible without deviating from the scope of the claims. In particular features of embodiments may be implemented separately or in combination. Also, different dimensions and materials may be selected for purpose specific endoscopes and the like. In particular, the skilled person will understand that the extensive use of glued parts entails low manufacturing costs, in turn rendering the endoscope suitable for single use. In this respect it should be noted that single use means the use involving one single patient, and in particular does not imply that the endoscope may only be used in one single procedure involving the person. It may thus very well be used repeatedly for the same or different procedures involved in an examination and/or treatment of a patient.

We claim:

1. A handle for an endoscope, said handle comprising:
a handle housing,
an operating member accommodated in said handle,
two guide tubes sized and configured to receive therethrough, respectively, a first part of a first pull wire and a first part of a second pull wire,
an anchoring block having a proximal surface spaced apart and opposite a distal surface, two bores each having a first opening in the proximal surface and a second opening in the distal surface, the first openings being closer to each other than the second openings, each of the two guide tubes passing through one or the other of the two bores, the anchoring block also having adhesive inlet passages intermediate the first opening and the second opening of each of the two bores, the adhesive inlet passages in fluid communication with each of the two bores, respectively, and a hardened adhesive securing the two guide tubes to the anchoring block at or adjacent to each of the adhesive inlet passages in predetermined positions relative to the operating member.

2. The handle of claim 1, wherein the two bores are through-bores, and wherein the two guide tubes extend through the through-bores.

3. The handle of claim 1, wherein the anchoring block comprises a single-piece of transparent plastic material.

4. The handle of claim 1, wherein the handle housing comprises a receptacle sized and configured to accommodate the anchoring block, and wherein the anchoring block is secured in the receptacle in a fixed position relative to the operating member.

5. The handle of claim 4, wherein the receptacle is formed integrally with the handle housing in one-piece.

6. The handle of claim 1, wherein the anchoring block comprises a first surface spaced apart and opposite a second surface, and a top surface spaced apart and opposite a bottom surface, and wherein the two bores are disposed between the first surface and the second surface and extend from the proximal surface to the distal surface.

7. The handle of claim 1, the handle housing further comprising a post having a recess on a free end of the post, the handle further comprising a bearing and an operating shaft, the bearing positioned in the recess of the post and having a blind cylindrical hole, the operating shaft having a first end positioned in the blind cylindrical hole of the bearing and connected to the operating member, whereby rotation of the operating member causes the first end to rotate in the bearing.

8. The handle of claim 7, wherein the post is flexible and the operating shaft is sufficiently long that after assembly the operating shaft causes the post to flex away from the operating member and tension resulting from such flexing of the post prevents lateral movement of the shaft.

9. The handle of claim 7, wherein the bearing is made from a material having a lower coefficient of friction than the post.

10. The handle of claim 1, the handle housing further comprising a first post and a second post, each of the first post and the second post having a recess on a free end thereof, the handle further comprising a first bearing, a second bearing, and an operating shaft connected to the operating member and rotating therewith, the first bearing positioned in the recess of the first post and having a blind cylindrical hole ending in a bottom, the second bearing positioned in the recess of the second post and having a blind cylindrical hole ending in a bottom, and the operating shaft having a length longer than a distance between the bottoms of the blind cylindrical holes before assembly of the operating shaft with the first bearing and the second bearing.

11. An endoscope comprising the handle of claim 1.

12. The endoscope of claim 11, wherein the endoscope is adapted for single use by adhesively bonding the two guide tubes to the anchoring block.

13. The endoscope of claim 11, further comprising pull wires including the first pull wire and a second pull wire, and wherein the pull wires passing through, respectively, the two guide tubes and the two bores.

14. A method of making an endoscope, the method comprising:
pivotally securing an operating member in a handle housing;
securing an anchoring block to the handle housing in a fixed position relative to the operating member, the anchoring block comprising a first bore and a second bore disposed at an angle to the first bore, a first surface spaced apart and opposite a second surface, and an inlet passage in fluid communication with the first bore, wherein the first bore and the second bore are disposed between the first surface and the second surface;
securing a first guide tube to the first bore and a second guide tube to the second bore;
securing a proximal part of a first pull wire extending proximally from the first guide tube to the operating member leaving a free end;
tensioning the free end; and
securing the free end to a portion of the first pull wire extending proximally from the first guide tube to the operating member.

15. The method of claim 14, further comprising, before securing the first guide tube to the first bore, cutting the first guide tube to uncover the proximal end of the first pull wire.

16. The method of claim 15, wherein securing a proximal part of a first pull wire extending proximally from the first guide tube to the operating member leaving a free end comprises looping the portion of the first pull wire extending proximally from the first guide tube to an attachment point of the operating member.

17. The method of claim 14, further comprising:
before securing the first guide tube to the first bore, cutting the first guide tube to uncover the proximal end of the first pull wire;
providing an adhesive to the inlet passage to secure the first guide tube to the anchoring block; and
wherein securing a proximal part of a first pull wire extending proximally from the first guide tube to the operating member leaving a free end comprises looping the portion of the first pull wire extending proximally from the first guide tube to an attachment point of the operating member.

* * * * *